United States Patent
Cromlish et al.

(10) Patent No.: US 6,329,137 B1
(45) Date of Patent: Dec. 11, 2001

(54) INTACT CELL ASSAY FOR PROTEIN TYROSINE PHOSPHATASES USING RECOMBINANT BACULOVIRUSES

(75) Inventors: Wanda Cromlish, Montreal; Brian Kennedy, Kirkland, both of (CA)

(73) Assignee: Merck Frosst Canada & Co., Quebec (CA)

( * ) Notice: Subject to any disclaimer, the term of this patent is extended or adjusted under 35 U.S.C. 154(b) by 0 days.

(21) Appl. No.: 09/519,773

(22) Filed: Mar. 7, 2000

Related U.S. Application Data (60) Provisional application No. 60/123,243, filed on Mar. 8, 1999.

(51) Int. Cl.$^7$ ............................... C12Q 1/68; C12Q 1/70; C12N 15/866; C12N 5/10

(52) U.S. Cl. .................................. 435/5; 435/6; 435/7.1; 435/7.2; 435/325; 435/7.21; 435/7.4; 435/29; 435/69.1; 435/455; 435/456; 435/348; 435/254.11; 435/7.72; 435/254.2; 435/320.1; 435/183

(58) Field of Search ........................... 435/5, 6, 7.1, 325, 435/7.2, 7.21, 7.4, 29, 69.1, 455, 456, 348, 254.11, 7.72, 254.2, 183, 320.1

(56) References Cited

FOREIGN PATENT DOCUMENTS

| | | |
|---|---|---|
| WO 91/13173 | 9/1991 | (WO) . |
| WO 94/03610 | 2/1994 | (WO) . |
| WO 95/06735 | 3/1995 | (WO) . |
| WO 95/07935 | 3/1995 | (WO) . |
| WO 95/09656 | 4/1995 | (WO) . |
| WO 96/40276 | 12/1996 | (WO) . |
| WO 98/04712 | 2/1998 | (WO) . |

OTHER PUBLICATIONS

Justement et al., Science, vol. 252, pp. 1839–1842, Jun. 1991.*
W. Cromlish, et al., Biochemical Pharmacology, vol. 58, pp. 1539–1546, 1999 "Development and Validation of an Intact Cell Assay for Protein Phosphatases Using Recombinant Baculoviruses".
Charbonneau H and Tonks NK, 1002 protein phosphatases? Annu Rev Cell Biol 8:463–493, 1992.
Neel BG and Tonks NK, protein tyrosine phosphatases in signal transduction, Current Opinions in Cell Biology 9: 193–204, 1997.
Trowbridge IS, Ostergaard HL & Johnson P, CD45: a leukocyte–specific member of the protein tyrosine phosphatase family, Biochim Biophys Acta 1095:46–56, 1991.
C. McFarland, et al., Correlation between src family member regulation by protein–tyrosine–phosphatase CD45 and transmembrane signaling through the T–cell receptor, Proc Natl Acad Sci 90: 1404–1406, 1993.

Lin J. Brown, et al., Regulation of Basil Tyrosine Phosphorylation of the B Cell Antigen Receptor Complex by the Protein Tyrosine Phosphatase, CD45, J Immunol 149:3182–3190, 1992.
Zhang, Protein–Tyrosine Phosphatases: Biological Function, Structural Characteristics and Mechanism of Catalysis, Critical Reviews in Biochemistry and Molecular Biology 33:1–52, 1998.
Cicirelli, et al., Microinjection of protein–tyrosine–phosphatase inhibits insulin action in Xenopus oocytes, Proc Natl Acad Sci 87:5514–5518, 1990.
Ahmad, et al., Osmotic loading of neutralizing antibodies demonstrates a role of protein–tyrosine–phosphatase–1B in negative regulation of the insulin action pathway, J Biol Chem 270: 20503–20508, 1995.
Seely, et al., Protein tyrosine phosphatase–1B interacts with the activated insulin receptor, Diabetes 45: 1379–1385, 1996.
Burke, et al., Potent Inhibition of Insulin Receptor Dephosphorylation by a Hexamer Peptide Containing the Phosphotyrosyl Mimetic F2Pmp, Biochem Biophy Res Commun 204: 129–134, 1994.
Cromlich, W. et al., Selective Inhibition of Cyclooxygenase–1 and –2 Using Intact Insect Cell Assays, Biochem Pharm 52: 1777–1785, 1996.
Summers, et al., A manual for Methods for Baculovirus Vectors and Insect Culture Procedures (Bulletin No. 1555). Texan A & M University, Texas Agricultural Exp. Station, College Station, TX 1987.
Huyer, et al., Mechanism of Inhibition of Protein–tyrosine Phosphatases by Vanadate and Pervanadate, J. Biol Chem 272: 843–851, 1997.
Yanagi S, et al., CD45 Modulates Phosphorylation of Both Autophosphorylation and Negative Regulatory Tyrosines of Lyn in B Cells, J Biol Chem 271: 30487–30492, 1996.

(List continued on next page.)

*Primary Examiner*—David Guzo
(74) *Attorney, Agent, or Firm*—James L. McGinnis; David L. Rose (57) ABSTRACT

The invention relates to an intact cell assay for direct quantitation of protein tyrosine phosphatase (PTP) activity using the baculovirus expression system. A PTP expressed in transformed host insect cells is processed and localized in their predicted subcellular compartments. Assays are performed on the PTP expressing host cells challenged with a substrate such as, p-nitrophenyl phosphate. This substrate is hydrolysed to p-nitrophenol by expressed phosphatase activity. Emergence of p-nitrophenol is determined spectrophotometrically and is a measure of PTP activity.

Further, the assay and transformed host cells of this invention are particularly useful in a screening method for selecting potential inhibitors to PTPs. Basically, transformed host cells are pre-incubated with or without inhibitors and the assay conducted as described. This invention relates to an intact cell assay with a direct readout of PTP activity that is useful in a cell-based screening method for selecting inhibitors of PTPs.

19 Claims, 8 Drawing Sheets

OTHER PUBLICATIONS

Sheng Z, et al., The Baculovirus Autographa californica encodes a Protein Tyrosine Phosphatase, J Biol Chem 268: 4728–4733, 1993.

Frangioni, et al., The nontransmembrane tyrosine phosphatase PTP–1B localizes to the Endoplasmic Reticulum via its 35 amino acid C–terminal sequence, Cell 68: 545–560, 1992.

McVicar, et al., Activation of peripheral large granular lymphocytes with the seine/threonine phosphatase inhibitor, okadaic acid, Eur J Immunol 24: 165–170, 1994.

Fujiki, et al., Tumor necrosis factor–alpha, a new tumor promoter, engendered by biochemical studies of okadaic acid, J Biochem (Tokyo) 115: 1–5, 1994.

Yu, et al., Okadaid acid, a serine/threonin phosphatase inhibitor, induces tyrosine dephosphorylation/inactivation of protein kinase FA/GSK–3 alpha in A431 cells, J Biol Chem 269: 14341–14344, 1994.

Lee, et al., Reversible Inactivation of Protein–tyrosine Phosphatase 1B in A431 Cells stimulated with Epidermal Growth Factor, J Biol Chem 273: 15366–15372, 1998.

Sundaresan M, et al., Requirement of generation of H2O2 for platelet–derived growth factor signal transduction, Science 270: 296–299, 1996.

Bae, et al., Epidermal growth factor (EGF)–induced generation of hydrogen peroxide. Role in EGF receptor–mediated tyrosine phosphorylation, J Biol Chem 272: 217–221, 1997.

Heffetz D. et al., The insulinomimetic agents H2O2 and vanadate stimulate protein tyrosine phosphorylation in intact cells, J Biol Chem 265: 2896–2902, 1990.

Li J. et al., Phenylation oxide and vanadate: apparent paradox of inhibition of protein phosphotyrosine phosphatases in rat adipocytes, Biochem Biophys Acta 1312: 223–230, 1996.

Swarup, et al., Inhibition of membrane phosphotyrosyl–protein phosphatase activity by vanadate, Biochem Biophys Res Comm 107: 1104–1109, 1982.

Heyliger, et al., Effect of vanadate on elevated blood glucose and depressed cardiac performance of diabetic rats, Science 227: 1474–1477, 1985.

Goldfine, et al., Metabolic effects of sodium metavanadate in humans with insulin–dependent and noninsulin–dependent diabetes melitus in vivo and in vitro studies, J Clin Endocrinol & Metab 80: 3311–3320, 1995.

Kadota, et al., Peroxides of vanadium: a novel and potent insulin–mimetic agent which activates the insulin receptor kinase, Biochem Biophys Res Comm 147: 259–266, 1987.

Fantus, et al., Pervanadate[peroxide(s) of vanadate] mimics insulin action in rat adipocytes via activation of the insulin receptor tyrosine kinase, Biochemistry 28: 8864–8871, 1989.

Posner, et al., Peroxovanadium compounds: A new class of potent phosphotyrosine phosphatase inhibitors which are insulin mimetics, J Biol Chem 269: 4596–4604, 1994.

Bevan, et al., Peroxovanadium compounds: biological actions & mechanism of insulin–mimesis, Mol Cell Biochem 153: 49–58, 1995.

Yale, et al., In vivo effects of peroxovanadium compounds in BB rats, Mol Cell Biochem 153: 181–190, 1995.

Elchebly, et al., Increased Insulin Sensitivity and Obesity Resistance in Mice Lacking the Protein Tyrosine Phosphatase–1B Gene.

* cited by examiner

| COMPOUND | PTP1B-FL | CD45-cat | CD45-FL | mock-infected |
|---|---|---|---|---|
| OUBAIN | nd | >1000 | nd | >1000 |
| OKADAIC ACID | nd | >6.7 | nd | >6.7 |
| $H_2O_2$ | 10.9 | 9.9 | 15.4 | nd |
| PHENYLARSINE OXIDE | 16.3 | 10.4 | 7.2 | nd |
| VANADATE | 0.29 | 0.07 | 0.06 | 1.6 |
| PERVANADATE | 0.02 | 0.01 | 0.004 | nd |
| $F_2$PMP PEPTIDE | 0.30 | >10 | >10 | >10 |

FIG. 6

INTACT CELL ASSAY FOR PROTEIN TYROSINE PHOSPHATASES USING RECOMBINANT BACULOVIRUSES

This application is based on and claims priority from, U.S. Provisional Application No. 60/123,243, filed Mar. 8, 1999, which is incorporated herein in its entirety.

BACKGROUND OF THE INVENTION

Protein tyrosine phosphatases (PTPs) (EC 3.1.3.48) dephosphorylate tyrosyl residues, acting in concert with protein tyrosine kinases (PTKs) to control tyrosine phosphorylation of proteins in the cell. This reversible phosphorylation at tyrosyl residues has been found in many signal transduction pathways, such as those involved in the action of growth factors, control of cellular proliferation, differentiation and metabolism (1, 2). Although PTPs are very different in size and structural organization, they contain a unique and highly conserved active site sequence (1,2,6). Representative examples of PTPs are CD45 and PTP1B. CD45, is a transmembrane receptor-type PTP that activates protein tyrosine kinase p56lck and p59fyn, and is involved in T cell (3,4) and B cell(5) signaling. PTP1B is a nonreceptor PTP containing a single catalytic domain and has been implicated in insulin-resistant states and type 2 diabetes (6,7–9).

Specific and selective PTP inhibitors have a potential value as biological tools to reveal the function of individual phosphatases in cellular signal transduction pathways and as disease-modulating drugs. To date, sodium orthovanadate (vanadate), pervanadate and phenylarsine oxide are known PTP inhibitors. None of these exhibit tyrosine phosphatase selectivity. Small peptides containing the hydrolytically stable difluorophosphonomethyl phenylalanine were found to be inhibitors of PTP1B (10). Available cell-based systems that can be used for the identification of a broad range of selective PTP inhibitors employ downstream readouts for the quantitation of PTP activity.

A limitation in this type of assay is that test inhibitors can interact at sites in the signal transduction pathway other than at the enzyme of interest, thus giving rise to an erroneous outcome, such as a false positive result for a test inhibitor. To date there are no known assays without intermediate steps, having an immediate end-point and that allow for a direct quantitation of PTP activity.

Previously, an in vitro intact cell assay for screening nonsteroidal anti-inflammatory drug inhibition of human cyclooxygenase was developed. The assay utilizes the baculovirus expression system in sf9 insect cells (11).

Consequently, one object of the present invention was to develop an assay for PTP activity that overcomes the defects in the prior art.

Another object was to provide an assay for PTP activity that is reliable and reproducible.

More particularly, an object of the present invention was to select cell-permeable PTP substrates such that the hydrolysis of these substrates provides a direct readout of the phosphatase activity.

These and other objects will become apparent to those of ordinary skill from the teachings provided herein.

The application refers to a number of publications, the content of which is hereby incorporated by reference in their entirety.

SUMMARY OF THE INVENTION

A method for assaying protein tyrosine phosphatase (PTP) activity in a eukaryotic host cell is disclosed comprising the steps of:

(a) transforming a host cell with a vector containing a nucleotide sequence encoding a PTP to provide a transformed host cell line;

(b) incubating said transformed host cell with a substrate to said PTP activity; and (c) comparing the amount of PTP activity in the transformed host cell to a standard.

BRIEF DESCRIPTION OF THE DRAWINGS

Having thus generally described the invention, reference will now be made to the accompanying drawings, showing by way of illustration a preferred embodiment thereof, and in which:

FIG. 1 shows Western blot analysis of PTP expression in sf9 cells as a function of time in total cell lysate and subcellular localization;

FIG. 3 shows the time course of hydrolysis of the substrate pNPP, by CD45-cat and PTP1B-FL expressed in intact sf9 cells. The extent of substrate hydrolysis by the phosphatase was determined by measuring the amount of p-nitrophenol formed spectrophotometrically at $OD_{405}$.

DETAILED DESCRIPTION

Protein tyrosine phosphatases are present in high amounts within cells. As a consequence, it is difficult to evaluate the activity of specific PTPases above the background of total cellular PTPases. PTPases have been overexpressed in mammalian cells (sometimes to the detriment of cellular function) using various overexpression systems. To date, the only way to discriminate between a specific PTPase of interest and all other cellular PTPases is to monitor a downstream readout parameter. For example, in the case of CD45, the amount of IL-2 secreted by Jurkat cells is an indication of the activity of this PTPase. This downstream readout may lead to the introduction of variables that may result in an erroneous outcome.

As used herein the term "transform", refers to a general term for the introduction of a nucleotide sequence into host cells including infecting host cells with a recombinant virus. A representative example is a baculovirus vector engineered with a nucleotide sequence of interest used to infect an insect cell for the expression of the peptide encoded by the nucleotide sequence.

The present invention concerns the development of a cell-based method for measuring the activity of a specific PTP. Particularly, the method relates to a direct measurement of PTP activity in a transformed eukaryotic host cell expressing exogenous PTP activity.

Accordingly the present invention provides a method to directly assay PTP activity, thus eliminating the effect of downstream variables.

Thus, the first embodiment of the present invention is directed to an intact cell assay for a PTP. The PTP of interest is expressed in transformed eukaryotic host cells, the transformed cells are incubated with a substrate and a direct measure of phosphatase activity is obtained.

In a particular preferred embodiment there is provided a eukaryotic host cell transformed with an appropriate expression vector having a nucleotide sequence encoding a PTP. The nucleotide sequence encoding PTP optionally includes any derivatives, variants or fragments capable of expressing the encoded PTP. All these are within the scope of this invention. In a non-limiting example representative PTPs selected for the purpose of this invention include CD45 and PTP1B having GenBank Accession numbers Y00062 and G190741, respectively (Hooft van Huijsduijnen, 1998, Gene 225:1–8). Other examples of PTPs useful for the purpose of this invention are listed in Hooft van Huijsduijnen (supra).

The eukaryotic host cells used for the transformation include mammalian, fungal (including yeast) and insect cells. In a particular embodiment, insect cells are the preferred host cells. Non-limiting examples of insect cells include sf21, sf9, High Five (BT1-TN-5B1-4), BT1-Ea88, Tn-368, mb0507, Tn mg-1, Tn Ap2, and whole insect larvae.

In a specific embodiment of this invention, the host cell is the insect cell sf9, which is transformed with appropriate insect cell recombinant virus. These recombinant viruses that are able to transform and infect an insect cell line are well known to a person skilled in the art and can be selected and used accordingly. These are all within the scope of this invention.

In a most preferred embodiment of this invention, the cell-based assay comprises sf9 insect cells transformed with a specific PTP recombinant baculovirus for the expression of the specific PTP by the sf9 cells.

In a further aspect, the substrates used for the purpose of this invention comprise compounds that are cell permeable and have a hydrolysable phosphate. Non-limiting examples include fluorescein monophosphate, fluorescin diphosphate, ELF 97 (obtained from Molecular Probes Inc.) and p-nitrophenyl phosphate (pNPP).

In an additional aspect of this invention, PTP activity can be evaluated either by a decrease in substrate concentration or an emergence of reaction product(s). Different means for detecting the result of the phosphatase activity include spectrophotometric, fluorescence, ELISA (enzyme linked immunoassay), RIA (radioimmunoassay) and radioactivity (by tagging the substrate).

Of the different substrates tried by the Applicant, the substrate, pNPP produced consistently reproducible and reliable results, with an endpoint that can be easily measured.

Therefore in a specific embodiment of this invention, the preferred substrate is pNPP. This substrate is cell permeable and is hydrolysed by PTP resulting in the product p-nitrophenol. As described above p-nitrophenol can be measured by means including spectrophotometric.

In a preferred embodiment the emergence of the product of pNPP, p-nitrophenol is measured spectrophotometrically.

According to another embodiment, the present invention provides a screening method to identify test compounds as inhibitors to PTP. Particularly, this invention provides a screening method for identifying PTP inhibitors that are cell permeable.

In this method, the assay of the present invention is performed in the presence or absence of a test compound and the amounts of hydrolysed substrate compared. A variance in the results may be an indication of the efficacy of a test compound as a candidate inhibitor to PTP.

Therefore, this invention provides a screening method for identifying a test compound as an inhibitor to PTP activity in a eukaryotic host cell, which comprises the steps of:
 a) incubating a eukaryotic host cell transformed with a vector containing a nucleotide sequence encoding a PTP in the presence of a PTP substrate and the test compound under conditions which effect PTP activity;
 b) incubating the eukaryotic host cell transformed with a vector containing a nucleotide sequence encoding a PTP in the absence of the test compound under conditions which effect PTP activity; and
 c) comparing the results of step (a) and step (b).

This invention further provides host cells transformed with nucleotide sequences encoding PTPs. These transformed hosts may be used in the methods and assays of this invention.

The methods and assays of the present invention, for measuring PTP activity can be comprised in a kit, such a kit includes: eukaryotic cells transformed with a vector containing a nucleotide sequence encoding PTP, substrate for PTP activity and appropriate buffers.

In an aspect of the present invention, the screening method can be scaled up and adapted for a highthroughput system. Such a system is useful for identifying an inhibitor to PTP for use as a research tool and for therapeutic applications in mammals in need of such therapy.

EXAMPLES

Cell Culture sf9 cells (Invitrogen, San Diego, Calif., U.S.A.) were cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (12).

Example 1

Construction of Recombinant Baculovirus Transfer Vectors

The cDNA for PTP1B came from Dr. R. L. Erikson, Harvard University, USA. The CD45 cDNA was obtained from Dr. Frank Jirik, University of British Columbia, Canada. The recombinant baculoviruses were prepared using the Bac-to-Bac Baculovirus Expression System (Gibco-BRL, Mississauga, Ontario, Canada). Briefly, the genes of interest were cloned into the pFASTBAC donor plasmid, which had been engineered to include a FLAG sequence at the 5' end of the cDNA. The FLAG sequence allows for easy identification and purification of the expressed protein of interest using the anti-FLAG M2 antibody (Intersciences Inc., Markham, Ontario). The resultant plasmids were transformed into competent DH10BAC $E. coli$ cells. Following transposition and antibiotic selection, the recombinant bacmid DNA was isolated from selected $E. coli$ colonies and then used to transfect sf9 insect cells. The virus found in the supernatant media was amplified three times up to a total viral stock volume of 500 mL.

Example 2

Production of Recombinant Proteins

Baculovirus infection of 500-mL spinner cultures of sf9 cells was done essentially as described by Summers and Smith (12). Sf9 cells at a density of $1-3 \times 10^6$ cells/mL were pelleted by centrifugation at 300 g for 5 min, the supernatant was removed, and the cells were resuspended at a density of $1 \times 10^7$ cells/mL in the appropriate recombinant viral stock (MOI of 10). Following gentle shaking for 1.5 hr at room temperature, fresh medium was added to adjust the cell density to $\sim 1 \times 10^6$ cells/mL and the cells were cultured in suspension at 28° C. for the indicated times, post-infection.

Example 3

Cellular Fractionation and Whole Cell Extracts from Infected sf9 Cells

At various times post-infection, aliquots of the infected cells were removed, and protein expression analyzed by SDS-PAGE and western blot analysis. Cellular fractionation was performed as follows. Infected sf9 cells were centrifuged at 300 g for 5 min and the pelleted cells washed with cold PBS. The cell pellets were then resuspended in 1 mL of cold 0.1 M Tris, pH 7.4, 5 mM EDTA and sonicated 3×10 sec on ice. Samples were centrifuged for 10 min at 500 g at 4° C. and the resulting supernatants retained. The pellets were resuspended in 1 mL of cold Tris/EDTA buffer, sonicated, and recentrifuged as described above. The two supernatant fractions were pooled and centrifuged at 4° C. for 60 min at 100,000 g. The microsomal pellets were resuspended by a 2-sec pulse sonication in 0.1 M Tris, pH 7.4, 5 mM EDTA.

Whole cell extracts were prepared from 1 mL aliquots of infected sf9 cells at the specified times post-infection. Pelleted cells (300 g, 5 min) were washed once in PBS (4° C.), resuspended in 50 µL of water and cell membrane disrupted by freezing and thawing the pelleted cells. Protein concentrations were determined using Coomasie Protein Assay Reagent Kit (Pierce, Rockford, Ill., USA) with bovine serum albumin as the standard.

Example 4

SDS-PAGE/Western Blot Analysis

The expression and production of specific protein, time course of expression and subcellular localization of the individual phosphatases from the recombinant baculovirus infected sf9 cells was determined by western blot analysis. Briefly, whole cell lysate and 100,000 g fractions (pellet or supernatant) were mixed with SDS sample buffer (60 mM Tris.Cl [6.8], 10% SDS, 6% glycerol, 5% β-mercaptoethanol, 0.05% bromophenol blue), heated to 95° C. for 4 min, and electrophoresed on 10% Tris-glycine acrylamide denaturing gels (Novex, San Diego, Calif., U.S.A.). Proteins were transferred electrophoretically to nitrocellulose membranes for 16 hr at 100 mA constant current using a Novex transfer apparatus. The membranes were reacted with the following antibodies.

FLAG M2 Antibody

The nitrocellulose membranes were blocked for 30 min with 5% powdered milk in 20 mM Tris-HCl, pH 7.5, 500 mM NaCl, 0.1% Tween 20, followed by 2 washes in the Tris/NaCl buffer containing (v/v) 1% Tween 20. The blots were then incubated with 1/2000 final dilution of FLAG M2 Antibody (Intersciences Inc., Markham, Ontario) in Tris/NaCl buffer. Immunoreactive proteins were visualized by using a 1/2000 dilution of anti-mouse Ig, horseradish peroxidase (Amersham, Oakville, Ontario) as the second antibody and development by ECL as described by the manufacturer (Amersham Life Science, Oakville, Ontario).

CD45 Antibody

The nitrocellulose membranes were blocked for 60 min with 5% powdered milk in 10 mM Tris-HCl, pH 7.5, 100 mM NaCl, 0.1% Tween20. The blots were immediately incubated with 1/500 dilution of anti-CD45 antibody (Transduction Laboratories, Lexington, Ky., U.S.A.) in blocking buffer for 1 h. Following 6 washes in Tris/NaCl buffer, the blots were incubated for 1 h with a 1/2000 dilution of anti-mouse Ig, horseradish peroxidase. The immunoreactive protein was visualized by ECL.

Figure 1A:
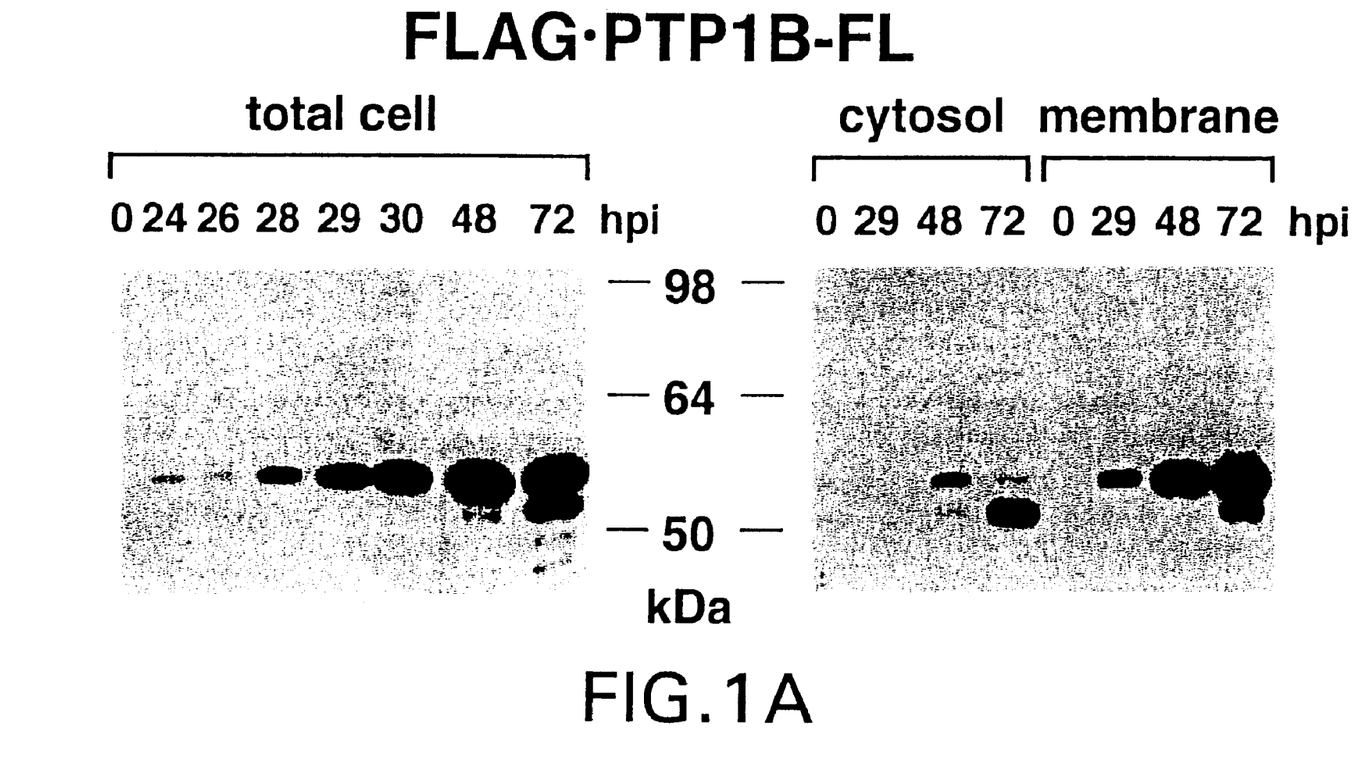
FIG. 1A shows the results of Sf9 cells infected with recombinant virus for FLAG-PTP1B-FL, at the designated hours post-infection (hpi), as shown at the top of the membrane, total cell lysate or 100,000 g cytosolic and membrane fractions were prepared. Proteins (6.5 µg/lane) from each of these preparations were separated by SDS-PAGE, transferred to nitrocellulose, immunoblotted with anti-FLAG M2 antibody and detected by chemiluminescence.

The results shown in FIG. 1A, indicate that FLAG-tagged PTP1B-FL (~52 kDa) is expressed by about 24 hpi, exponentially increases between 26 and 48 hpi, and then begins to be cleaved or degrade by 72 hpi. PTP1B-FL is present in the membrane fraction of the sf9 cells at about 29 hpi and by about 48 hpi it appears intact in the cytosol. However, by about 72 hpi, a 50 kDa cleavage product predominates in the cytosol while the higher molecular weight form remains present in the membrane fraction.

Figure 1B:
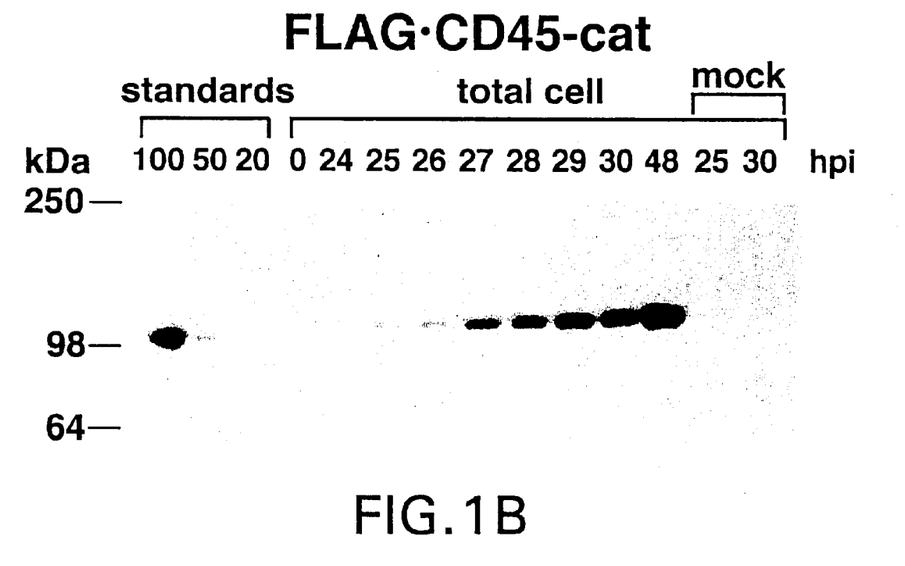
FIG. 1B shows the results of Sf9 cells infected with recombinant virus for FLAG-CD45-cat, at the designated hours post-infection (hpi), total cell lysates or 100,000 g cytosolic and membrane fractions were prepared. Proteins (6.5 µg/lane) from each of these preparations were separated by SDS-PAGE, transferred to nitrocellulose, immunoblotted with anti-FLAG M2 antibody and detected by chemiluminescence. Standards are 20, 50 and 100 ng of FLAG-CD45-cat purified from bacteria.

The expression pattern of FLAG-tagged CD45-cat is very similar to that of PTP1B and is shown in FIG. 1B. The protein is observed beginning at about 24 hpi with an apparent molecular weight of 98 kDa and continues to be exponentially expressed to about 48 hpi. Extracts from the mock-infected (HCOX-1) sf9 cells at 25 and 30 hpi, as expected show no FLAG M2 antibody cross reacting with any proteins. Since FLAG affinity purification on the M2 antibody column yields CD45-cat protein in the supernatant fraction of lysed cells (data not shown), it is postulated that the recombinant FLAG-tagged CD45-cat is localized in the cytosol of sf9 cells.

Figure 1C:
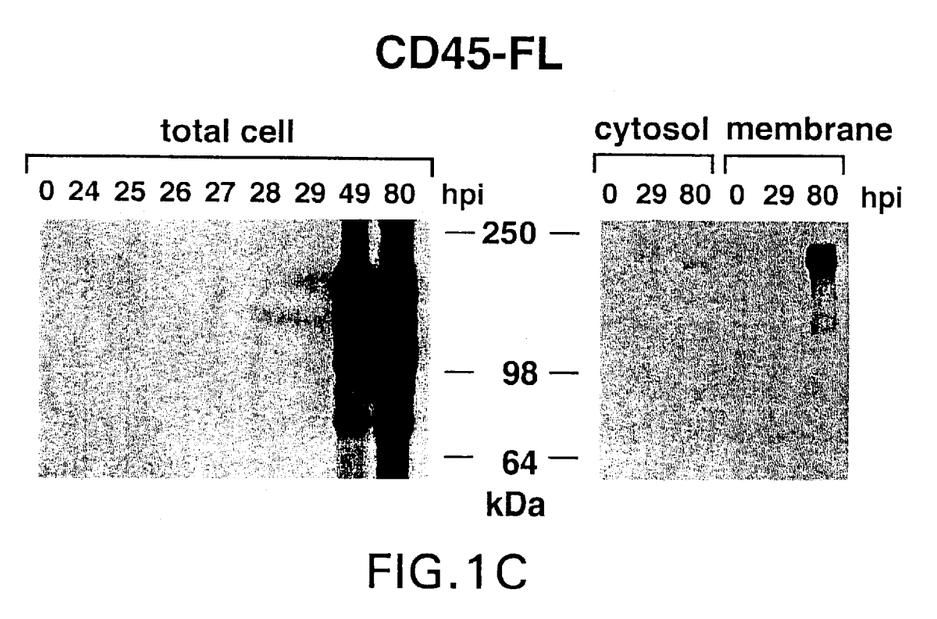
FIG. 1C shows the results of Sf9 cells infected with recombinant virus for CD45-FL, at the designated hours post-infection (hpi), total cell lysates or 100,000 g cytosolic and membrane fractions were prepared. Proteins (6.5 µg/lane) from each of these preparations were separated by SDS-PAGE, transferred to nitrocellulose, immunoblotted with anti-CD45 antibody and detected by chemiluminescence.

The expression of the full length CD45 shown in FIG. 1C, is significantly lower than that of the other two phosphatases, presumably reflecting the membrane localization of this protein. CD45-FL is just visible at about 29 hpi in whole cell extract. At later time points of infection, about 49 and 80 hpi, the ~150 kDa protein species predominates, but presumably many proteolytic degradation products cross react with the anti-CD45 transmembrane antibody, especially when protein gels are overloaded as is the case of the later timepoints. When infected cells are fractionated at about 29 hpi there is no visible CD45-FL, however at about 80 hpi the full length protein is clearly visualized intact and non-degraded, and as expected appears to be localized mainly in the microsomal fraction.

Results of the western analysis demonstrate that the PTPs are expressed at various but detectable levels at about 29 hpi. Further evaluation of the infected sf9 cells by trypan blue at this time point, indicate that the cells are still highly viable and demonstrating that the development of a cell-based assay for PTPs activity is feasible.

Example 5
Intact Cell Assay Development

Sf9 cells were infected with PTP1B-FL, CD45-FL, CD45-cat or HCOX-1 (11) (mock-infected) recombinant baculovirus. Infected cells were collected 29 hpi by centrifugation in Beckman GS-6R at 460 rpm (48 g) for 5 min, washed once in assay buffer (Hanks' solution buffered with 15 mM Hepes, pH 7.4 (Sigma, St. Louis, Mo., U.S.A.)) and recentrifuged at 300 rpm (21 g) for 10 min. The cells were gently resuspended in assay buffer and examined using a hemacytometer for cell density and viability by trypan blue exclusion. Assays were performed using a Tomtec Quadra 96 pipeting robot, programmed to mix gently after each addition as follows. Aliquots of $2 \times 10^5$ PTP expressing cells in 200 µL of Hanks' solution were dispensed into each well of 96-well polypropylene plates and pre-incubated either with inhibitor or DMSO vehicle (3 µL) for 15 min at 37° C. The pre-incubated cells were challenged with different concentrations of tissue culture grade pNPP (Sigma-Aldrich Canada Ltd., Oakville, Ontario) for 15 min then pelleted by centrifugation for 3 min at 410 g and 4° C. Aliquots of 100 µL of supernatant were transferred to fresh clear polystyrene 96-well plates and the amount of hydrolysis product determined spectrophotometrically at $OD_{405}$. Phosphatase activity attributed to the recombinant PTP is the difference in the amount of pNPP hydrolysis between the PTP expressing and mock-infected cells.

Initial characterization of the PTP insect cell-based assays was carried out at 29 hpi using PTP1B-FL and CD45-cat recombinant baculoviruses. Although many substrates were analyzed (data not shown), pNPP was chosen for its consistent and reproducibile results. The rate of hydrolysis of pNPP, as measured spectrophotometrically at $OD_{405}$, correlated with substrate concentration, time of substrate challenge, cell number, viral titer and final tyrosine phosphatase protein expression. Using $2 \times 10^5$ PTP-expressing cells/well and varying the concentration of pNPP between 0 and 50 mM, the hydrolysis of the substrate by PTP1B-FL and CD45-cat during a 15 minute incubation followed very similar profiles.

Figure 2:
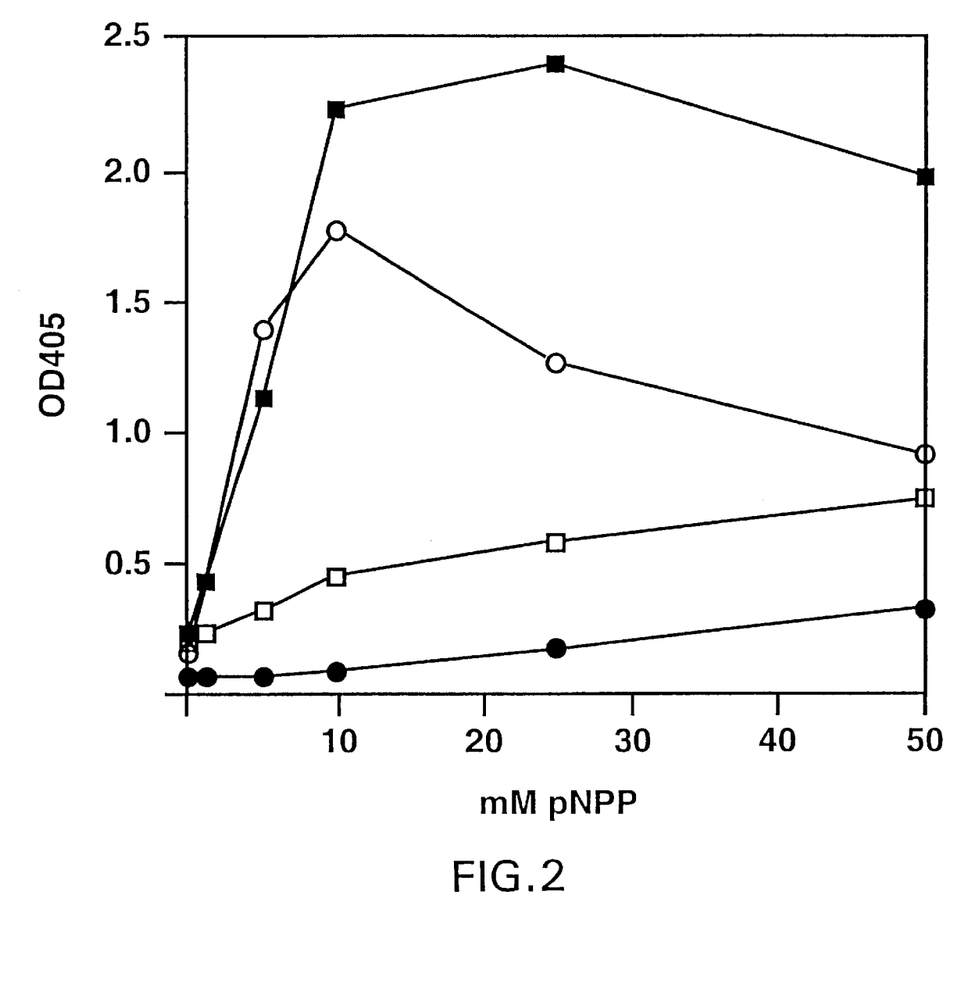
FIG. 2 shows the hydrolysis of p-nitrophenyl phosphate (pNPP) substrate by intact sf9 cells infected with recombinant baculovirus, FLAG-PTP1B-FL, FLAG-CD45-cat and hCOX-1 (mock-infected). At 29 hpi, infected sf9 cells expressing FLAG-PTP1B-FL (■), FLAG-CD45-cat(○) and mock-infected(□) were challenged with 0, 1, 5, 10, 25 and 50 mM of pNPP for 15 min. Phosphatase activity was determined directly by measuring the amount of p-nitrophenol formed spectrophotometrically at $OD_{405}$. The absorbance of various concentrations of pNPP in the absence of cells is also shown (●).

FIG. 2 illustrates typical pNPP hydrolysis patterns of these two phosphatases. In the absence of cells, increasing concentrations of pNPP led to a slight increase in the baseline absorbance at $OD_{405}$. Mock-infected (HCOX-1) cells contain background levels of PTPs and therefore exhibit increased hydrolysis of substrate with increasing substrate concentration. Sf9 cells infected with either PTP1B-FL or CD45-cat recombinant virus showed marked hydrolysis of pNPP at low substrate concentration with maximal levels of substrate utilization occurring at 10 mM pNPP for PTP1B-FL and CD45-cat. The window between PTP hydrolysis and mock-infected cells represents the amount of substrate utilization due to the recombinant tyrosine phosphatase.

Figure 3A:
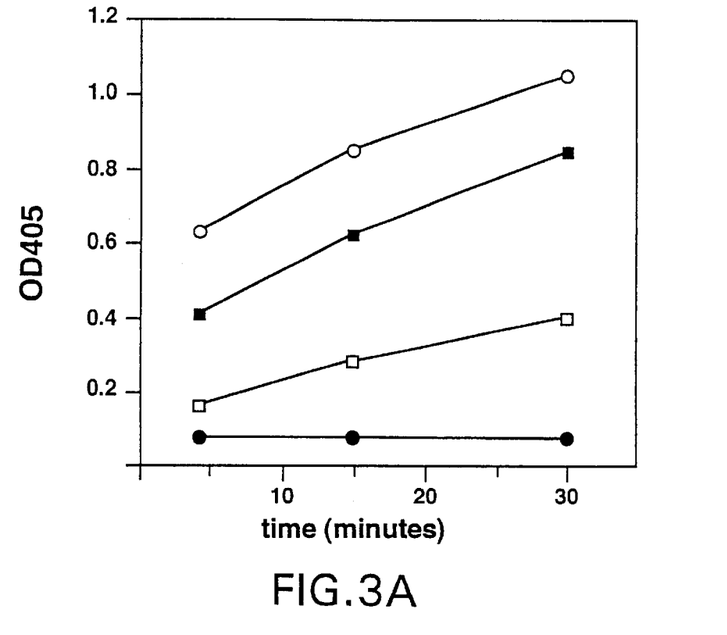
FIG. 3a shows the absorbance of p-nitrophenol at 29 hpi in sf9 cells expressing FLAG-CD45-cat challenged with 0(●), 5(□), 10(■) or 50(○) mM pNPP for 15 min.
Figure 3B:
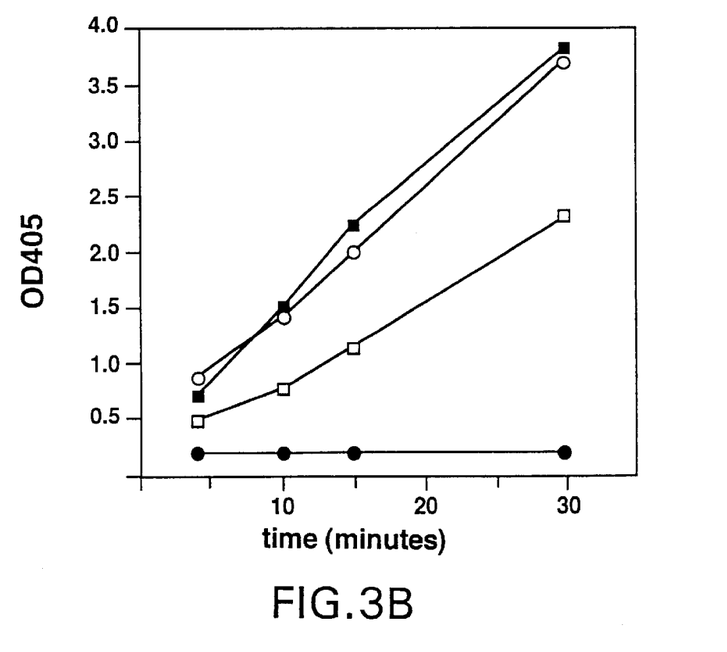
FIG. 3b shows the absorbance of p-nitrophenol at 29 hpi in sf9 cells expressing FLAG-PTP1B-FL challenged with 0(●), 5(□), 10(■) or 50(○) mM pNPP for 15 min.

FIG. 3, shows the time course of different concentrations of pNPP hydrolysis by sf9 cell expressing CD45-cat or PTP1B-FL. The hydrolysis appears to be linear with respect to time, irrespective of substrate concentration or phosphatase present in the sf9 cells.

Figure 4:
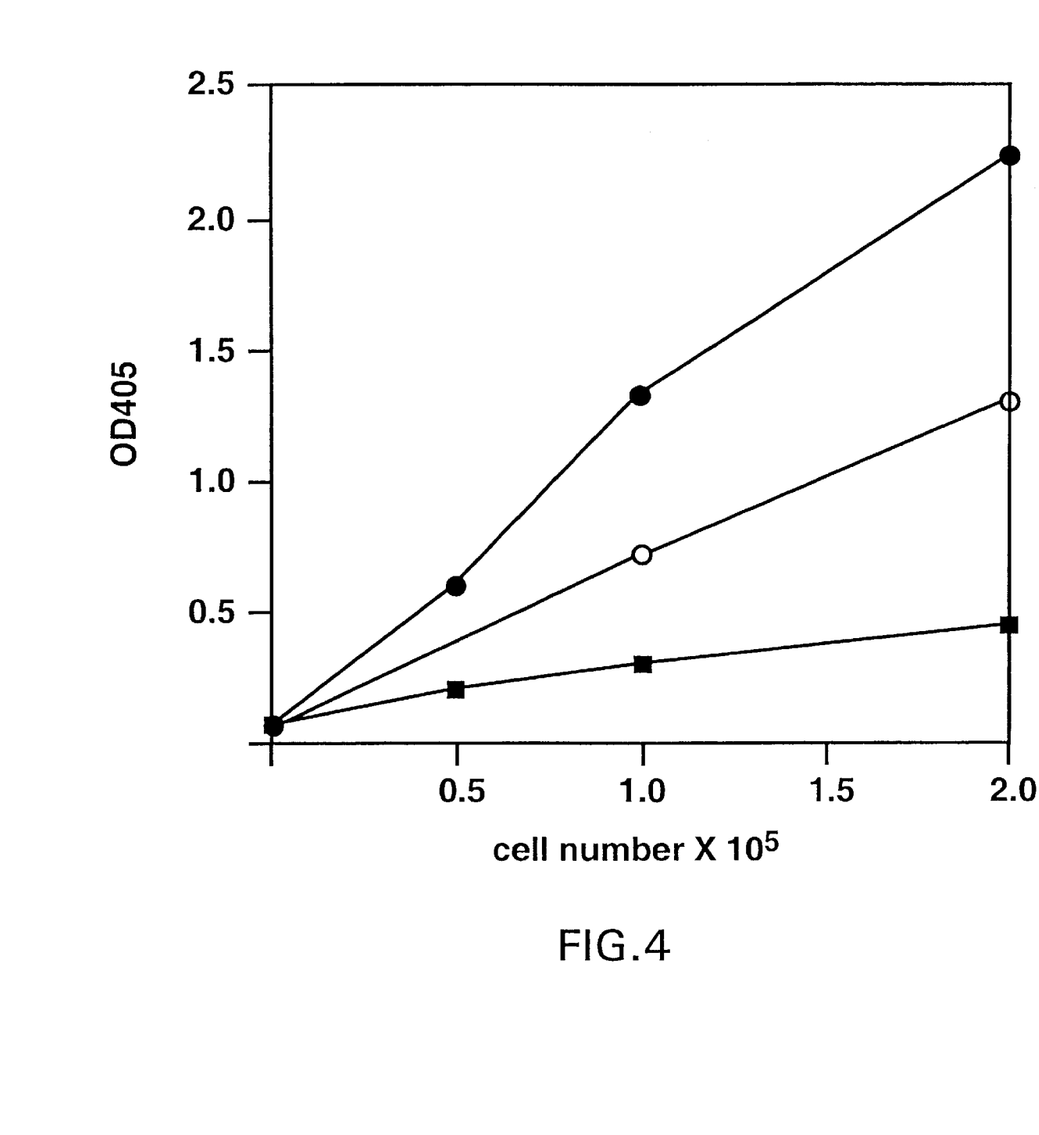
FIG. 4 shows the substrate hydrolysis profiles of intact sf9 cells infected with recombinant CD45-cat, PTP1B-FL or hCOX-1(mock) baculovirus as a function of assay cell number. FLAG-PTP1B-FL (●), FLAG-CD45-cat(○) or hCOX-1(■) infected sf9 cells were challenged with 10 mM pNPP for 15 min and the amount of hydrolyzed substrate was determined by measuring the amount of p-nitrophenol formed at $OD_{405}$.

FIG. 4 demonstrates that in this assay the rate of substrate hydrolysis is linear with respect to cell number.

Figure 5:
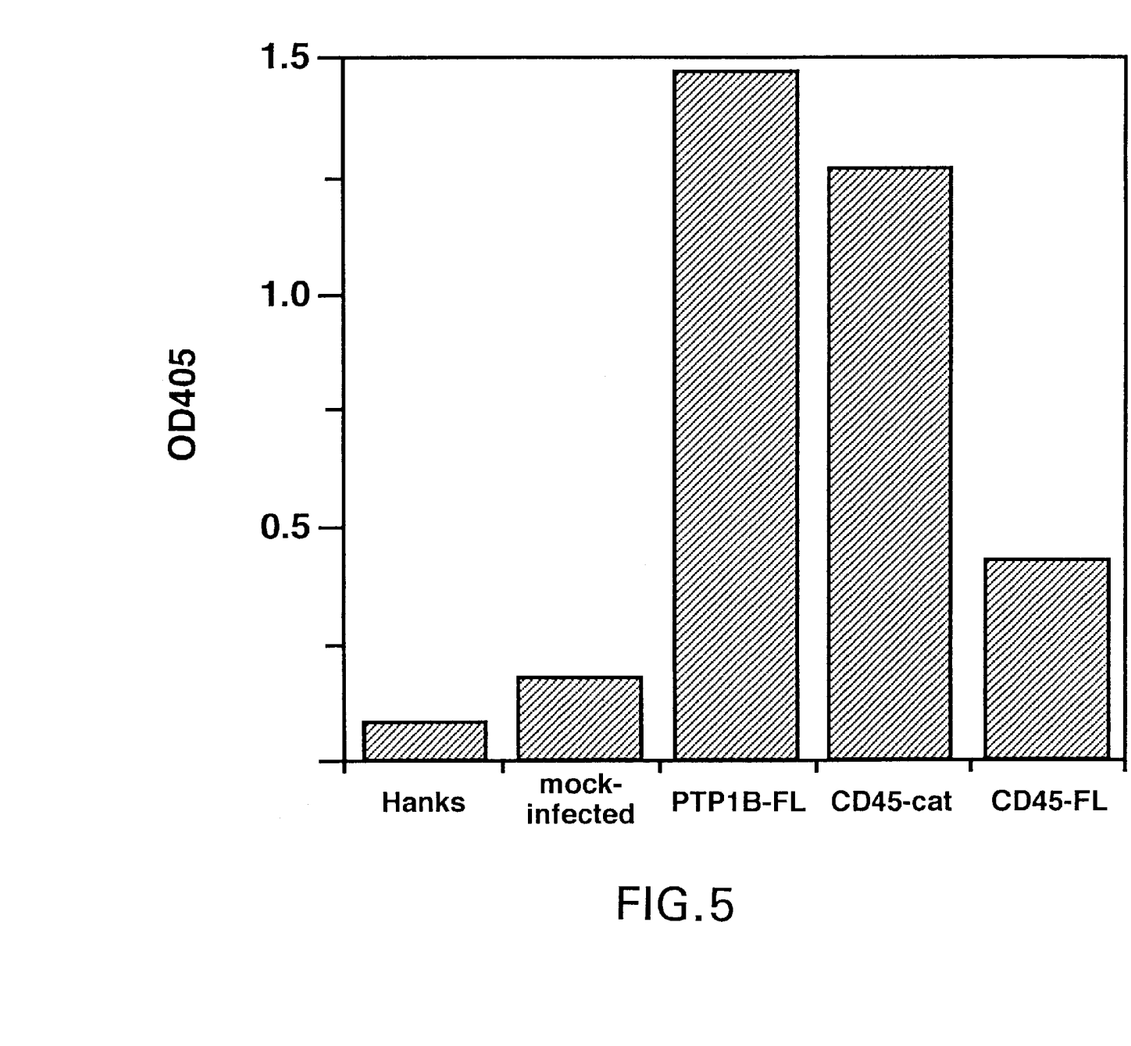
FIG. 5 shows a typical substrate hydrolysis profiles of intact sf9 cells infected with recombinant PTP1B-FL, CD45-cat, CD45-FL or hCOX-1 (mock) baculovirus. Infected cells harvested 29 hpi were washed and resuspended in Hanks'/Hepes. Aliquotes of $2\times10^5$ cells/well were challenged with 10 mM pNPP for 15 min and the amount of p-nitrophenol formed was detected at $OD_{405}$.

A summary of the total output of PTP activity is shown in FIG. 5. Intact uninfected sf9 cells, challenged with 10 mM pNPP have a basal level of phosphatase activity as shown by the increase in the absorbance at 405 when compared to 10 mM pNPP/Hanks alone. Intact sf9 cells infected with PTP1B-FL, CD45-cat and CD45-FL have significantly increased rate of pNPP hydrolysis of 8.3, 7.1 and 2.4 fold respectively when compared to mock-infected cell (background). These levels of phosphatase activity correlate with the relative amount of protein visualized at 29 hpi in western blot analysis (FIG. 1), with the level of expression being the highest in PTP1B-FL followed by CD45-cat and CD45-FL. In the case of PTP1B-FL and CD45-cat, the amount of pNPP hydrolyzed by enzymes inside the intact sf9 cells represents ~30% of the total hydrolysis that can occur if the cells are disrupted and the enzymes released to be in direct contact with the substrate (data not shown).

The following conditions for subsequent experimentation were used. Infected sf9 cells expressing either PTP1B-FL, CD45-cat or CD45-FL are harvested at 29 hpi by gentle centrifugation and resuspended in Hepes-buffered Hanks' solution, pH 7.4 at 37° C. An aliquot of $2 \times 10^5$ PTP-infected cells are challenged with a final concentration of 10 mM pNPP for 15 min, centrifuged at 4° C. and the amount of substrate hydrolysis determined spectrophotometerically at $OD_{405}$.

Example 6
Inhibitor Titration and Characterization

The inhibition of PTP activity was determined by comparing the amount of pNPP hydrolyzed in the presence of an inhibitor and in the DMSO treated PTP expressing cells. Briefly, potential inhibitors are preincubated with infected sf9 cells for 15 min prior to a 15 min challenge with 10 mM pNPP.

The inhibitors studied include ouabain (Sigma-Aldrich Canada, Oakville, Ontario), an inhibitor of Na—K ATPase known also to exhibit p-nitrophenyl phosphatase activity; okadaic acid (Gibco-BRL, Gaithersburg, Md., U.S.A.), a known serine/threonine phosphatase inhibitor; 30% $H_2O_2$ (Aldrich), phenylarsine oxide (Sigma, St. Louis, Mo., U.S.A.), vanadate, and pervanadate. Vanadate and pervanadate were prepared as described (13). This represents four known protein tyrosine phosphatase inhibitors. The difluorophosphonomethyl phenylalanine containing peptide inhibitor, a potent and selective PTP1B-FL inhibitor obtained from the Merck sample collection.

Figure 6:
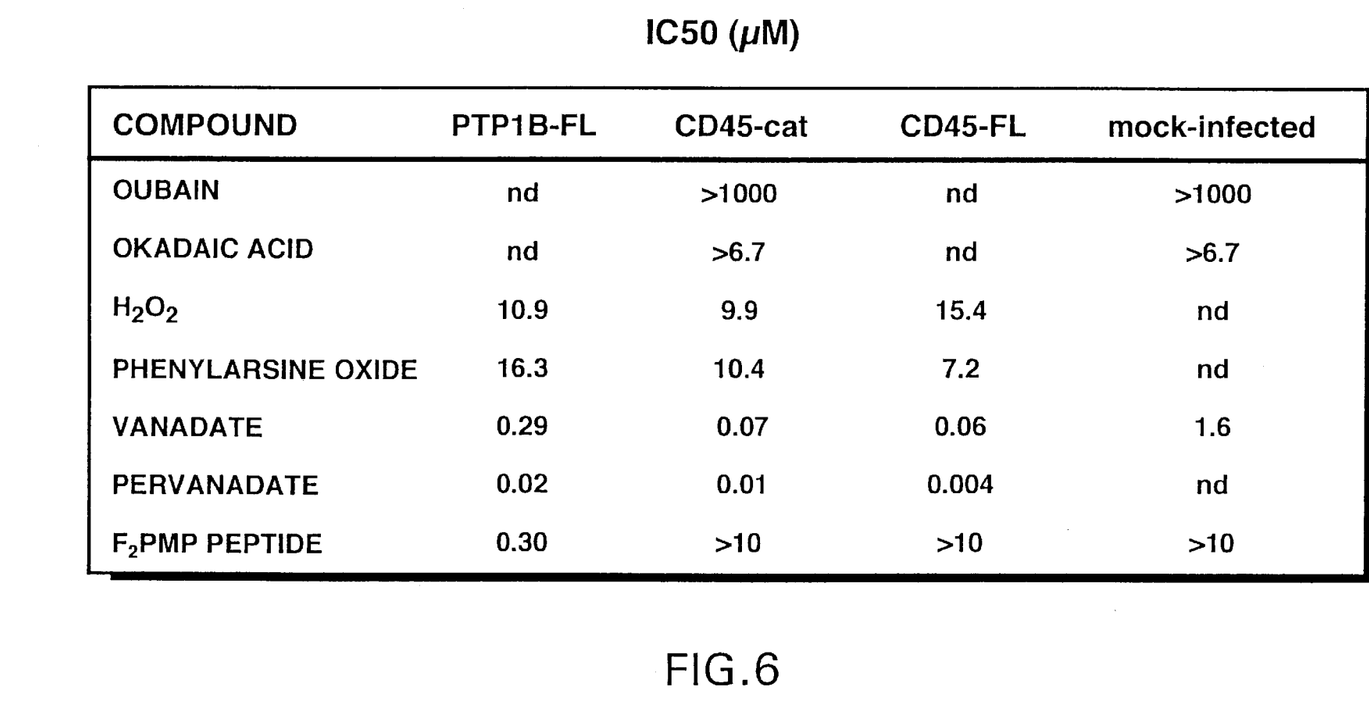
FIG. 6 shows the $IC_{50}$ values of known inhibitors on the activity of the PTPs; PTP1B-FL, CD45-cat and CD45-FL, and hCOX-1 (mock) expressed in the insect cells sf9 at 29 hpi. The infected cells were washed and resuspended in Hank's/Hepes buffer (pH 7.4) at 37° C., and pre-incubated with different concentrations of the indicated inhibitor for 15 min. These pre-incubated cells were then challenged with 10 mM pNPP substrate and the amount of the hydrolysis product, p-nitrophenol, was measured spectrophotometrically at $OD_{405}$.

FIG. 6 tabulates the results of the potency and selectivity of the tested inhibitors. Neither ouabain at 1 mM or okadaic acid at 6.7 μM had any effect on the CD45-cat or background phosphatases in infected sf9 cells. As predicted, hydrogen peroxide and phenylarsine oxide showed limited potency and selectivity with $IC_{50}$ values in the range of 7–16 μM. Vanadate is not very potent on background tyrosine phosphatases in mock-infected sf9 cells with an $IC_{50}$ of 1.6 μM, but appears to be very effective at inhibiting the expressed PTPs with slightly greater selectivity (4.5×) towards CD45 than PTP1B-FL. Of the tested compounds, pervanadate appears to be the most potent inhibitor of CD45 and PTP1B-FL with $IC_{50}$ values between 5–20 nM. Pervanadate is a general term for a variety of complexes formed between vanadate and hydrogen peroxide. Pervanadate inhibits PTPs by the irreversible inactivation of the active site cysteine, a mechanism distinct from the competitive inhibitory nature of vanadate (13). The diflurophosphonomethyl phenylalanine peptide is a proprietary compound that has been found to inhibit PTP1B-FL with an $IC_{50}$ of 0.3 μM, a value that is similar to that of vanadate. This compound, however, is 33-fold more selective for PTP1B-FL than CD45-FL, CD45-cat or background phosphatases found in mock-infected sf9 cells.

Discussion

The role of protein tyrosine phosphatases (PTPs) in the modulation of signal transduction by tyrosine-kinase containing receptors and oncogene products has been gaining more investigational attention. PTP1B, a cytosolic non-receptor PTP, is one of the first PTPs identified and is implicated in the regulation of the insulin signaling pathway (7–9). CD45 is a transmembrane receptor-type PTP expressed on all hematopoietic cells except erythrocytes (14), is required for normal T and B cell signaling (3,4,5). Thus, inhibition of PTP1B or CD45 could potentially have therapeutic benefits in the areas of NIDDM or immunosuppression, respectively. The successful development of intact sf9 cell-based assays for COX-1 and COX-2 (11) that could identify potent and isozyme selective NSAIDs prompted us to investigate the use of the baculovirus system again. In order to define potent, selective and cell-permeable inhibitors for intracellular phosphatases, a cell-based assay utilizing sf9 cells infected with specific PTP recombinant baculoviruses was developed.

An alternative method for discriminating between the activity of a PTP of interest and endogeneous phosphatase activity is monitoring downstream readout parameter. For example, in the case of CD45, the amount of IL-2 secreted by Jurkat cells can be used as a measure of the activity of this PTP. As documented previously (11) and the results presented in this study show, the baculovirus expression system can be developed into cell-based assays for use in drug screening. We describe here a "mix and read" intact cell assay for the activity of specific protein tyrosine phosphatase, which eliminates potential interference of downstream sites in the signal transduction pathway when evaluating a test compound. The PTP of interest is overexpressed in sf9 cells for a short period of time which is not detrimental to cellular function, challenged with an inhibitor then a substrate and direct read out of inhibition is obtained. Thus, the advantage of such a cell-based assay is that there are no intermediate steps between PTP enzyme inhibition and the endpoint readout. Using intact sf9 cells expressing PTP1B or CD45, we have characterized known PTP inhibitors, as well as, demonstrated that the assay can identify potent and highly selective compounds inhibitory for a PTP of interest.

The sf9 insect cell line used in the baculovirus expression system is derived from the ovarian tissue of the fall armyworm Spodoptera (12). Infection of this cell line with recombinant baculoviruses for PTP1B and CD45 results in the expression of these proteins.

The genome of the baculovirus *Autographa californica* encodes a 19 kDa protein tyrosine phosphatase (15). Sf9 cells appear to offer the cellular environment and factors necessary for both PTP1B and CD45 phosphatase activity. The cellular localization of the expressed PTPs was as expected, since the catalytic domain of CD45 (CD45-cat) does not contain a transmembrane domain as the full length CD45, it was expressed at high concentrations in cytosolic fractions. CD45-FL is found to be minimally expressed (as compared to the general expression level of many proteins) in the membrane fraction of sf9 cells, this is probably due to the fact that it is a transmembrane protein and therefore proceeds through the Golgi prior to insertion into the plasma membrane. The level of expression of the full length form of CD45 at 29 hpi is the same as that found in an equivalent number of Jurkat cells, which express very high amounts of CD45 per cell surface area (data not shown). The full length PTP1B is anchored to the endoplasmic reticulum at its C-terminal (16). PTP1B-FL is expressed at very high levels and found to be associated with the membrane fraction at early time points post-infection. At about 48 hpi, a time when the viability of the infected cells begins to decline, PTP1B-FL is found in the cytosol and at greater than 72 hpi, a 50 kDa N-terminal fragment appears both in the membrane and cytosolic fractions. This is presumably due to proteolytic breakdown of the protein. The demonstration that the expressed PTPs are found in the expected cellular location provides an advantage for drug screening. Proper compartmentalization may be necessary for PTP specificity of cellular substrate and selectivity of some potential inhibitors based on intracellular drug distribution.

It was important to identify an appropriate time point for this assay, ie; harvesting the recombinant cells at a timepoint when a sufficient amount of PTP is produced and the cells remain healthy and viable (prior to the deleterious effects associated with later stages of viral infection). The infected sf9 cells are harvested at 29 hpi, a timepoint when each of the PTPs is fully post-translationally modified, properly targeted and active.

The cells expressing the appropriate PTP were assayed in 96-well plates and mechanization was facilitated using the Tomtec Quadra 96 pipetting device.

The effect of inhibitors on PTP activity is a measure of the change in the hydrolysis of para-nitrophenyl phosphate (pNPP) when compared to a control. Different substrates were tested, pNPP yielded the most consistent results.

The uptake of phosphate is important and vital in the metabolic requirements of growth and replication in eukaryotic cells. The substrate, pNPP, is presumed to be taken up into the sf9 cells by a phosphate transporter. The assay demonstrates that the rate of hydrolysis of pNPP correlates well with the viral titer used to infect the sf9 cells, as well as, cell number and substrate concentration. Further, the window of phosphatase activity between the PTP of interest and the background activity in mock-infected cells correlates with amount of protein expressed. Of the three PTPs tested PTP1B-FL and CD45-cat were most highly expressed with a 6 and 5-fold window of pNPP hydrolysis activity, respectively. CD45-FL was barely detected by Western and concomitantly showed a 1.5-fold window of activity.

The profiles of the inhibitors shown in FIG. 6, demonstrated sigmoidal shaped $IC_{50}$ curves in this assay.

Na—K-ATPase is known to exhibit pNPP hydrolyzing activity. To demonstrate that the amount of p-nitrophenol detected in the present assay was due to phosphatase activity, ouabain, an inhibitor of Na—K-ATPase, was tested and showed no inhibition up to 1 mM for both the background infected cells and CD45 expressing cells. Serine/threonine phosphatases do not hydrolyse pNPP since okadaic acid (17–19) had no effect. $H_2O_2$ has been shown to inactivate recombinant PTP1B in vitro by oxidizing its catalytic site cysteine (20). Direct exposure of cells to $H_2O_2$ activates signal transduction pathways by increasing protein tyrosine phosphorylation (21–23). The testing of $H_2O_2$ in our cell-based assay indeed showed that non-selective inhibition of PTP1B or CD45 in the $IC_{50}$ range of 10–15 $\mu$M is obtained. Phenylarsine oxide is a documented membrane permeable inhibitor of protein phosphotyrosine phosphatases (24), the results confirm that it is a non-potent, non-selective inhibitor of PTP1B and CD45 expressed within sf9 cells. Vanadate is a general PTP inhibitor (25) found to be competitively and reversibly bound at the active site (13) with insulin-mimetic properties (26), and in human clinical trials its been shown to be potentially useful in treating NIDDM (27). Vanadate was chosen to validate the assay described herein. It was found to be more potent than $H_2O_2$ and phenylarsine oxide at inhibiting the expressed phosphatases and appears to be slightly more selective for CD45 than PTP1B. Pervanadate, a complex of vanadate and $H_2O_2$, is also an insulin-mimetic and is documented as being more potent at increasing the levels of cellular tyrosine phosphorylation (28–32). It was found to be an irreversible inhibitor of PTP1B (13). Our data correlates and substantiates these observations. Pervanadate was 7–15 times more potent than vanadate in inhibiting CD45 and PTP1B expressed in the sf9 cell assay, though this inhibition is non selective. PTP inhibitors have value as biological research tools in the understanding of signal transduction pathways and as therapeutic agents with the potential of treating diseases and conditions needing the inhibition of specific protein tyrosine phosphatases.

In a successful application of this invention, the screening effort has uncovered a test compound, diflurophosphonomethyl phenylalanine. This compound containing peptide is cell permeable and >33-fold selective, potent PTP1B inhibitor. This compound is a nonhydrolyzable phosphotyrosine mimic, which functions as a competitive inhibitor at the catalytic site.

The baculovirus expression system can supply recombinant protein for enzymatic characterization, X-ray crystallographic studies, in vitro purified enzyme and microsomal assays and as reported previously (11) and here, reliable cell-based assays. The PTP1B and CD45 assays presented herein are mere representative examples of PTPs. It is the intent of the Applicant, that this assay be used for any PTP. Therefore, this invention encompasses any PTP for the purpose of providing an opportunity to uncover potentially useful inhibitors to a PTP that may be useful as a research tool and in the treatment of many yet to be identified therapeutic targets.

REFERENCES

1. Charbonneau H and Tonks N K, 1002 protein phosphatases? *Annu Rev Cell Biol* 8: 463–493, 1992.
2. Neel B G and Tonks N K, Protein tyrosine phosphatases in signal transduction, *Current Opinions in Cell Biology* 9: 193–204, 1997.
3. Trowbridge I S, Ostergaard H L and Johnson P, CD45: a leukocyte-specific member of the protein tyrosine phosphatase family, *Biochim Biophys Acta* 1095: 46–56, 1991.
4. Cahir McFarland E D, Hurley T R, Pingel J T, Sefton B M, Shaw A and Thomas M L, Correlation between src family member regulation by protein-tyrosine-phosphatase CD45 and transmembrane signaling through the T-cell receptor, *Proc Natl Acad Sci* 90: 1402–1406, 1993.
5. Lin J, Brown V K and Justement L B, Regulation of Basal Tyrosine Phosphorylation of the B Cell Antigen Receptor Complex by the Protein Tyrosine Phosphatase, CD45, *J Immunol* 149: 3182–3190, 1992.
6. Zhang Z Y, Protein-Tyrosine Phosphatases: Biological Function, Structural Characteristics and Mechanism of Catalysis, *Critical Reviews in Biochemistry and Molecular Biology* 33: 1–52, 1998.
7. Cicirelli M F, Tonk N F, Diltz C D, Weiel J E, Fischer E H and Krebs E G, Microinjection of protein-tyrosine-phosphatase inhibits insulin action in Xenopus oocytes, *Proc Natl Acad Sci* 87: 5514–5518, 1990.
8. Ahmad F, Li P M, Meyerovitch J and Goldstein B J, Osmotic loading of neutralizing antibodies demonstrates a role of protein-tyrosine-phosphatase-1B in negative regulation of the insulin action pathway, *J Biol Chem* 270: 20503–20508, 1995.
9. Seely B L, Staubs P A, Reichart D R, Berham P, Milarski K L, Salteil A R, Kusari J and Olefsky J M, Protein tyrosine phosphatase-1B interacts with the activated insulin receptor, *Diabetes* 45: 1379–1385, 1996.
10. Burke T R, Kole H K and Roller P P, Potent Inhibition of Insulin Receptor Dephosphorylation by a Hexamer Peptide Containing the Phosphotyrosyl Mimetic F2Pmp, *Biochem Biophys Res Commun* 204: 129–134, 1994.
11. Cromlish W and Kennedy B, Selective Inhibition of Cyclooxygenase-1 and -2 Using Intact Insect Cell Assays, *Biochem Pharm* 52: 1777–1785, 1996.
12. Summers M D and Smith G E, A manual for *Methods for Baculovirus Vectors and Insect Culture Procedures* (Bulletin No. 1555). Texas A & M University, Texas Agricultural Experiment Station, College Station, Tex., 1987.
13. Huyer G, Lui S, Kelly J, Moffat J, Payette P, Kennedy B, Tsaprailus G, Gresser M J and Ramachandran C, Mechanism of Inhibition of Protein-tyrosine Phosphatases by Vanadate and Pervanadate. *J Biol Chem* 272: 843–851, 1997.
14. Yanagi S, Sugawara H, Kurosaki M, Sabe H, Yamamura H and Kurosaki T, CD45 Modulates Phosphorylation of Both Autophosphorylation and Negative Regulatory Tyrosines of Lyn in B Cells, *J Biol Chem* 271: 30487–30492, 1996.
15. Sheng Z and Charbonneau H, The Baculovirus *Autographa californica* encodes a Protein Tyrosine Phosphatase, *J Biol Chem* 268: 4728–4733, 1993.
16. Frangioni J V, Beahm P H, Shifrin V, Jost C A and Neel B G, The nontransmembrane tyrosine phosphatase PTP-1B localizes to the Endoplasmic Reticulum via its 35 amino acid C-terminal Sequence, *Cell* 68: 545–560, 1992.
17. McVicar D W, Mason A T, Bere E W and Ortaldo J R, Activation of peripheral large granular lymphocytes with the seine/threonine phosphatase inhibitor, okadaic acid, *Eur J Immunol* 24: 165–170, 1994.
18. Fujiki H and Suganmura M, Tumor necrosis factor-alpha, a new tumor promoter, engendered by biochemical studies of okadaic acid, *J Biochem* (Tokyo) 115: 1–5, 1994.
19. Yu J S and Yang S D, Okadaic acid, a serine/threonine phosphatase inhibitor, induces tyrosine dephosphorylation/inactivation of protein kinase FA/GSK-3 alpha in A431 cells, *J Biol Chem* 269: 14341–14344, 1994.
20. Lee S-R, Kwon K-S, Kim S-R and Rhee S G, Reversible Inactivation of Protein-tyrosine Phosphatase 1B in A431 Cells stimulated with Epidermal Growth Factor, *J Biol Chem* 273: 15366–15372, 1998.

21. Sundaresan M, Yu Z-X, Ferrans, V J, Irani K and Finkel T, Requirement of generation of H2O2 for platelet-derived growth factor signal transduction, *Science* 270: 296–299, 1996.
22. Bae Y S, Kang S W, Seo M S Baines I C, Tekle E, Chock P B and Rhee S G, Epidermal growth factor (EGF)-induced generation of hydrogen peroxide. Role in EGF receptor-mediated tyrosine phosphorylation, *J Biol Chem* 272: 217–221, 1997.
23. Heffetz D, Bushkin I, Dror R and Zick Y, The insulinomimetic agents H2O2 and vanadate stimulate protein tyrosine phosphorylation in intact cells, *J Biol Chem* 265: 2896–2902, 1990.
24. Li J, Elberg G and Shechter Y, Phenylarsine oxide and vanadate: apparent paradox of inhibition of protein phosphotyrosine phosphatases in rat adipocytes, *Biochim Biophys Acta* 1312: 223–230, 1996.
25. Swarup G, Cohen S and Garbers D L, Inhibition of membrane phosphotyrosyl-protein phosphatase activity by vanadate, *Biochem Biophys Res Comm* 107: 1104–1109,1982.
26. Heyliger C E, Tahiliani A G and McNeil J H, Effect of vanadate on elevated blood glucose and depressed cardiac performance of diabetic rats, *Science* 227: 1474–1477, 1985.
27. Goldfine A B, Simonson D C, Folli F, Path M E and Kahn C R, Metabolic effects of sodium metavanadate in humans with insulin-dependent and noninsulin-dependent diabetes melitus in vivo and in vitro studies, *J Clin Endocrinol & Metab* 80: 3311–3320, 1995.
28. Kadota S, Fantus I G, Deragon G, Guyda H J, Hersh B and Posner B I, Peroxides of vanadium: a novel and potent insulin-mimetic agent which activates the insulin receptor kinase, *Biochem Biophys Res Comm* 147: 259–266, 1987.
29. Fantus I G, Kadota S, Deragon G, Foster B and Posner B I, Pervanadate[peroxide(s) of vanadate] mimics insulin action in rat adipocytes via activation of the insulin receptor tyrosine kinase, *Biochemistry* 28: 8864–8871, 1989.
30. Posner B I, Faure R, Burgess J W, Bevan A P, Lachance D, Zhang-Sun G, Fantus I G, Ng J B, Hall D A, Lum B S and Shaver A, Peroxovanadium compounds. A new class of potent phosphotyrosine phosphatase inhibitors which are insulin mimetics, *J Biol Chem* 269: 4596–4604, 1994.
31. Bevan A P, Drake P G, Yale J-F, Shaver A and Posner B I, Peroxovanadium compounds: biological actions & mechanism of insulin-mimesis, *Mol Cell Biochem* 153: 49–58, 1995.
32. Yale J-F, Vigeant C, Nardolillo C, Chu Q, Yu J-Z, Shaver A and Posner B I, In vivo effects of peroxovanadium compounds in BB rats, *Mol Cell Biochem* 153: 181–190, 1995.

What is claimed is:

1. A method for assaying protein tyrosine phosphatase (PTP) activity in an intact eukaryotic host cell comprising the steps of:
    (a) transforming a host cell with a vector containing a nucleotide sequence encoding a PTP to provide a transformed host cell line;
    (b) incubating said transformed host cell with a substrate to said PTP activity, wherein said substrate is cell permeable and is hydrolyzed by said PTP activity; and
    (c) directly measuring the PTP activity in hydrolyzing said substrate in the transformed host cell.

2. A method of claim 1 wherein said vector is a recombinant baculovirus expressing said PTP.

3. A method for identifying a test compound as an inhibitor of PTP activity in an intact eukaryotic host cell comprising the steps of:
    (a) incubating an intact eukaryotic host cell transformed with a vector containing a nucleotide sequence encoding a PTP in the presence of a PTP substrate and a test compound under conditions which effect PTP activity, wherein said substrate is cell permeable and is hydrolyzed by said PTP activity, and directly measuring the PTP activity in hydrolyzing said substrate in the transformed host cell;
    (b) incubating an intact eukaryotic host cell transformed with a vector containing a nucleotide sequence encoding a PTP in the presence of a PTP substrate in the absence of the test compound under conditions which effect PTP activity, wherein said substrate is cell permeable and is hydrolyzed by said PTP activity, and directly measuring the PTP activity in hydrolyzing said substrate in the transformed host cell; and
    (c) comparing the results of step (a) and step (b).

4. A method of claim 2 wherein said vector is a recombinant baculovirus expressing said PTP.

5. The method of claim 3, wherein said eukaryotic host cell is an insect cell line.

6. The method of claim 5, wherein said PTP is selected from PTP1B and CD45.

7. The method of claim 6 wherein said substrate is p-nitrophenyl phosphate and is hydrolysed to p-nitrophenol by said PTP activity.

8. The method of claim 7, wherein said p-nitrophenol is measured by spectrophotometric, radioactive, fluorescence or immunological means.

9. The method of claim 8, wherein said measurement is spectophotometric.

10. A eukaryotic host cell transformed with a nucleotide sequence encoding a specific PTP selected from CD45 and PTP1B wherein said host cell comprises p-nitrophenyl phosphate as a substrate, wherein said p-nitrophenyl phosphate is cell permeable and is hydrolyzed by said PTP activity.

11. The host cell according to claim 10, selected from the group consisting of insect cells, mammalian cells, fungi and yeast cells.

12. The host cell according to claim 11, wherein said host cell is an insect cell.

13. The host cell according to claim 12, wherein said PTP is CD45.

14. The host cell according to claim 12, wherein said PTP is PTP1B.

15. A kit for directly assaying protein tyrosine phosphatase (PTP) activity in a eukaryotic host cell including:
    (a) a host cell transformed with a vector containing a nucleotide sequence encoding a PTP,
    (b) positive and negative control reagents for said PTP activity, and
    (c) a p-nitrophenyl phosphate substrate to said PTP activity in an appropriate buffer.

16. A kit as recited in claim 15, wherein said vector is a recombinant baculovirus expressing said PTP.

17. The kit as recited in claim 16, wherein said eukaryotic host cell is an insect cell line.

18. The kit as recited in claim 17, wherein said PTP is selected from PTP1B and CD45.

19. The kit as recited in claim 17, wherein said PTP is PTP1B.

* * * * *